(12) United States Patent
Takahashi et al.

(10) Patent No.: US 8,175,809 B2
(45) Date of Patent: May 8, 2012

(54) FLUORESCENCE ANALYZING METHOD, FLUORESCENCE ANALYZING APPARATUS AND IMAGE DETECTING METHOD

(75) Inventors: Satoshi Takahashi, Hitachinaka (JP); Takashi Irie, Musashimurayama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1088 days.

(21) Appl. No.: 11/806,318

(22) Filed: May 31, 2007

(65) Prior Publication Data
US 2007/0281315 A1 Dec. 6, 2007

(30) Foreign Application Priority Data
May 31, 2006 (JP) .................................. 2006-150883

(51) Int. Cl.
G01N 33/48 (2006.01)
C12Q 1/68 (2006.01)
G06G 7/58 (2006.01)
G06F 7/60 (2006.01)

(52) U.S. Cl. .................... 702/19; 435/6; 702/20; 703/2; 703/11

(58) Field of Classification Search .................... None
See application file for complete search history.

(56) References Cited

U.S. PATENT DOCUMENTS

| | | | |
|---|---|---|---|
| 5,459,325 | A | 10/1995 | Hueton et al. |
| 6,090,555 | A | 7/2000 | Fiekowsky et al. |
| 7,139,415 | B2 | 11/2006 | Finkbeiner |
| 2005/0287549 | A1 | 12/2005 | Nagai et al. |
| 2009/0009756 | A1 | 1/2009 | Yamamichi et al. |

FOREIGN PATENT DOCUMENTS

| | | |
|---|---|---|
| JP | 9-503308 | 3/1997 |
| JP | 2000-69998 | 3/2000 |
| JP | 2001-255328 | 9/2001 |
| JP | 2002-181708 | 6/2002 |
| JP | 2002-286643 | 10/2002 |
| JP | 2005-514589 | 5/2005 |
| JP | 2005-283556 | 10/2005 |
| JP | 2005-345353 | 12/2005 |
| JP | 2006-006274 | 1/2006 |
| WO | WO 96/02824 | 2/1996 |
| WO | WO 2005/010210 A2 | 2/2005 |

OTHER PUBLICATIONS

Braslavsky, I., et al., "Sequence information can be obtained from single DNA molecules", PNAS, Apr. 1, 2003, pp. 3960-3964, vol. 100, Issue 7, www.pnas.oeg/cgi/doi/10.1073/pnas.0230489100.
Japanese Office Action issued in Japanese Patent Application No. JP 2006-150883, dated Aug. 11, 2009.

*Primary Examiner* — Shubo Zhou
(74) *Attorney, Agent, or Firm* — McDermott Will & Emery LLP (57) ABSTRACT

A fluorescence analyzing method includes the steps of irradiating a board, to which oligonucleotide is fixed, with light for fluorescence measurement; focusing produced fluorescence to form an image; and detecting the fluorescence with a two-dimensional sensor. Here, the board is provided with plural regions to which the oligonucleotide is fixed, and the plural regions are spaced apart from one another on the board substantially equidistantly in the vertical and horizontal directions. A fluorescent image is detected in a condition where the following equation is satisfied:

$$dd = ds \times M/n$$

where ds denotes the interval between the regions, M denotes the imaging magnification of an optical focusing/imaging system, dd denotes the pixel pitch of the two-dimensional sensor, and n denotes an integer (n=1, 2, 3, 4, 5).

10 Claims, 6 Drawing Sheets

| | RANDOMLY FIXED | EQUIDISTANTLY FIXED |
|---|---|---|
| IMMOBILIZED STATE | MEASURED DNA MOLECULES — RANDOMLY FIXED on BOARD | EQUIDISTANTLY FIXED on BOARD |
| AVERAGE INTERVAL | 1 $\mu$m | 1 $\mu$m |
| DETECTION RESOLUTION | 0.1 $\mu$m | 0.5 $\mu$m |
| REQUIRED NUMBER OF PIXELS | 100 PIXELS PER MOLECULE | 4 PIXELS PER MOLECULE |

FLUORESCENCE ANALYZING METHOD, FLUORESCENCE ANALYZING APPARATUS AND IMAGE DETECTING METHOD

BACKGROUND OF THE INVENTION

1. Field of the Invention

The present invention relates to an image detecting method. For example, the present invention relates to a method and an apparatus which capture fluorescence-labeled oligonucleotide in plural positions on a plane, and which then detect a fluorescence intensity and a fluorescence pattern on the basis of the captured oligonucleotide.

2. Description of the Related Art

The techniques of analyzing DNA, RNA, protein and so on are important in the fields of medicine, biology and the like, including gene analysis and gene diagnosis. Particularly in recent years, attention has been given to a method and an apparatus for simultaneously examining and analyzing various types of DNA sequence information and genetic information from one analyte, by using a DNA microarray (also defined as various names, such as an oligochip, a DNA chip and a biochip, which will be hereinafter collectively called a "DNA microarray"). The DNA microarray is formed by using a glass board or the like, which is divided into plural regions (e.g., several hundreds of regions to several tens of millions of regions), each of which is provided with a target DNA probe (generally, the DNA probes are of different types) immobilized thereon to form a minute reaction region. When the reaction region is caused to react with an analyte, an object DNA in the analyte is hybridized with, and captured by the immobilized DNA probe. When a fluorescence probe or the like is further bonded to the target DNA, fluorescence intensity or the like can be measured to determine a bonded state (i.e., a bonded position, which means a hybridized sequence) and the amount of bonding. The measurement results can be utilized for gene diagnosis, sequencing and so on.

An apparatus similar to a microscope (e.g., a confocal fluorescence microscope) generally called a "scanner" is used for reading the fluorescence intensity of the DNA microarray (e.g., JP-A No. Hei 9-503308 and JP-A No. 2000-69998). This apparatus irradiates the array with a minute spot beam of excitation light, such as laser light, then separates emitted fluorescence from the excitation light by using a spectroscope such as an interference filter, and then detects the fluorescence intensity by means of a photodetector such as a photomultiplier tube. In this event, the apparatus can determine the distribution of fluorescence intensity throughout the array, that is, the degree of bonding to each DNA probe, by two-dimensionally scanning the relevant minute spot formed on the array by use of a galvanometer mirror or the like, or by two-dimensionally scanning the array with the position of the minute spot fixed. Methods of reading the fluorescence intensity of the DNA microarray include, in addition to the above beam scanning, the method for irradiating the regions of the array with excitation light over a wide range, and then detecting a emitted fluorescent image by means of a two-dimensional camera (e.g., JP-A No. 2002-181708 and JP-A No. 2001-255328). The each region having the DNA probe immobilized is divided into several tens of sub regions, and the fluorescent intensity of the sub regions are detected. And regions except DNA probe immobilized regions are divided into sub regions.

In these methods, the detection of the fluorescence on the plural regions each having the DNA probe immobilized thereon involves making measurements on the array as divided into several tens of regions, and making measurements on each of the regions as subdivided. This makes it possible to detect the fluorescence on the regions as isolated from one another, even in a case where the plural reaction regions are misaligned. However, the number of pixels required for the two-dimensional sensor is several hundreds or more times the number of regions to be measured.

Determining of DNA, RNA sequencing is also an important technique. Samples are generally prepared in advance by labeling, with fluorescence, DNA fragments or groups of DNA fragments used in sequencing, and a molecular weight pattern in separation and expansion is measured and analyzed after electrophoretic migration or in electrophoretic migration. Specifically, a well-known Sanger method is used for inducing a dideoxy reaction, prior to the electrophoresis. Oligonucleotide with about 20 bases long, complementary to a known portion of a base sequence of sample DNA to be analyzed, is synthesized and labeled with a fluorophore. This oligonucleotide is used as a primer to form a complementary chain bond with about 1 picomole of the sample DNA, and thus yielding polymerase, which in turn induces a complementary chain extension reaction. Here, four types of deoxynucleotide triphosphates, namely, dATP, dCTP, dGTP and dTTP, as well as ddATP, for example, are added as substrates. When ddATP is captured with the complementary chain extension, no further extension of the complementary chain takes place. Thus, the fragments of varying lengths terminating with adenine (A) are prepared. For the above reaction, ddCTP, ddGTP and ddTTP are added in place of ddATP to induce reactions. The primers used in the each reactions have the same base sequence, are labeled with four types of fluorophores each of which can be spectroscopically identified. When the above four types of reactants are mixed, fragments with up to several hundreds of bases long and of lengths varying base by base, which fragments are complementary to the sample DNA, are obtained as labeled with the four types of fluorophores varying depending on the type of terminal base. The fragments are separated with a resolving power of one base, by capillary gel electrophoresis. The obtained samples migrate while being separated, and are irradiated with laser in order from the shortest sample. When fluorescence emissions are spectroscopically measured by using plural filters, the types of terminal bases of all fragments can be determined in order from the shortest fragment, on the basis of the temporal change in the fluorescence intensities of the respective four types of fluorescent substances.

Recently proposed is an approach of fixing DNA or the like to a board for sequencing, as described in Proc. Natl. Acad. Sci. (Proceedings of National Academy of Sciences), USA, vol. 100 (7), pp. 3960, 2003. With this approach, sequencing is performed by randomly capturing, molecule by molecule, fragments of sample DNA to be analyzed on a surface of the board, then inducing extension for substantially every base, and then detecting results thereof by fluorescence measurement. Specifically, sequencing of the sample DNA is performed by repeating a cycle including the steps of: inducing a DNA polymerase reaction, by using four types of dNTP derivatives (MdNTP) with detectable labels, which are captured as substrates of DNA polymerase in template DNA, and which can terminate a DNA chain extension reaction with the presence of a protecting group; then detecting the captured MdNTP on the basis of fluorescence or the like; and then returning the MdNTP to an extension-capable state. Since this technique allows sequencing of DNA fragments molecule by molecule, the technique makes it possible to concurrently analyze many fragments. Hence, analysis throughput can be increased. Since this method may possibly make it possible to perform sequencing by DNA single molecule, the method may possibly eliminate a problem inherent in the prior art, that is, the need to refine or amplify sample DNA for cloning, PCR or the like. Thus, speedy genome analysis and gene diagnosis can be expected. In the method, the molecules of the fragments of the sample DNA to be analyzed are randomly fixed on the surface of the board. For this reason, the method requires an expensive camera having the number of pixels that is several hundreds of times the number of the trapped molecules of the DNA fragments. Specifically, when the molecules of the DNA fragments are adjusted as spaced apart from one another at average intervals of 1 micron, some molecules are spaced apart from one another at greater intervals, and others are spaced apart at smaller intervals. Consequently, in order to detect the molecules as isolated from one another, fluorescent intensities need to be detected at a minute interval (example, <0.1 μm). Generally, resolution of measuring fluorescent image must be several tenth of the interval between the DNA molecules.

SUMMARY OF THE INVENTION

The aforementioned optical system requires the number of pixels, which is several hundreds or more times the number of regions, that is, the number of molecules of DNA fragments where the molecules are trapped on the board. For this reason, the optical system has a problem that detection speed slows down, and that an expensive two-dimensional sensor is required. Moreover, since fluorescent images need to be detected with a higher resolving power, there is another problem with increased costs for the system in which a condenser lens with a large numerical aperture (NA) needs to be used.

An object of the present invention is to provide a method for efficiently detecting an image with a small number of pixels, such as a method for efficiently detecting an image with a small number of pixels, when a two-dimensional sensor is used to detect a fluorescent image from molecules of DNA fragments trapped on a board. Another object of the present invention is to provide a method for detecting an image at low costs or with easy operation, for example, when a two-dimensional sensor is used to detect a fluorescent image from molecules of DNA fragments trapped on a board.

The present invention relates to, for example, an image detecting method, in which plural targets to be measured are precisely located, and then an image of each of the plural targets is formed on a specified pixel of a detector including plural detecting pixels. The present invention provides a fluorescence analyzing method including the steps of irradiating a board, to which oligonucleotide is fixed, with light for fluorescence measurement; focusing produced fluorescence to form an image; and detecting the fluorescence with a two-dimensional sensor. Here, the board is provided with plural regions to which the oligonucleotide is fixed, and the plural regions are spaced apart from one another on the board substantially equidistantly in the vertical and horizontal directions. Moreover, the fluorescent image is detected with a condition where the following equation is satisfied:

$$dd = ds \times M/n$$

where ds denotes the interval between the regions, M denotes the imaging magnification of an optical focusing/imaging system, dd denotes the pixel pitch of the two-dimensional sensor, and n denotes an integer (n=1, 2, 3, 4, 5).

The present invention provides another fluorescence analyzing method including the steps of irradiating a board, to which oligonucleotide is fixed, with light for fluorescence measurement; focusing produced fluorescence to form an image; and detecting the fluorescence with a two-dimensional sensor. Here, the board is provided with plural regions to at least a part of which the oligonucleotide is fixed, and which are spaced apart from one another on the board substantially equidistantly in the vertical and horizontal directions, and each single oligonucleotide molecule is fixed to at least a part of the plural regions. Moreover, the fluorescent image is detected with a condition where the following equation is satisfied:

$$dd = ds \times M/n$$

where ds denotes the interval between the regions, M denotes the imaging magnification of an optical focusing/imaging system, dd denotes the pixel pitch of the two-dimensional sensor, and n denotes an integer (n=1, 2, 3, 4, 5).

More preferably, the fluorescent image is detected with the above equation adjusted to satisfy the following equation: $dd = ds \times M/n$, where n=2, 3.

The interval ds between the regions for fixing the oligonucleotide preferably ranges between 100 nm and 10000 nm inclusive, and more preferably, between 500 nm and 1500 nm inclusive.

Preferably, the region, to which the oligonucleotide is fixed, has a diameter of 100 nm or less.

Preferably, it is effective to form a film substance having an optical shield function on a reaction region of a surface of the board, except for the plural regions to which the oligonucleotide is fixed. A metal film or the like is formed by vapor deposition or the like.

Preferably, the method includes a mechanism for adjusting the imaging magnification M to satisfy the equation, $dd = ds \times M/n$. Moreover, register markers are provided respectively to at least two positions on the board. The mechanism has a function unit for detecting the register markers and automatically adjusting the imaging magnification M.

The present invention makes it possible to reduce the number of pixels required for the two-dimensional sensor without impairing the accuracy in measurement. For example, the number of pixels can be reduced from several hundred times the number of regions to be measured to which oligonucleotide is fixed, to thirty or less times the number of regions, or further to ten or less times the number of regions. Thus, measurement can be performed efficiently. Accordingly, in a case where the same two-dimensional sensor is used, fluorescent images can be concurrently obtained from a larger number of regions, and thereby high throughput can be achieved. In a case where a camera having a small number of pixels is used, measurement can be performed more inexpensively.

For example, for the same number of molecules to be measured, the present invention allows efficient detection with a small number of pixels, and hence makes it possible to reduce the price of the two-dimensional sensor. Moreover, optical resolution can be made substantially equivalent to each interval between the regions to which oligonucleotide is fixed. Thus, a condenser lens with a large numerical aperture does not need to be used, and a low-priced lens can be used. In addition, it is not necessary to use an immersion lens, and thus the operation can be made easier.

DETAILED DESCRIPTION OF THE INVENTION

The present invention will be described below with reference to embodiments. However, it is to be understood that the present invention is not limited to these embodiments.

First Embodiment

A description will be given of an apparatus and a method for sequencing fragments of sample DNA by equidistantly trapping, molecule by molecule, fragments of the sample DNA to be analyzed on a surface of a board; inducing extension for substantially every base; and then detecting, for one molecule at a time, captured fluorescence labels. Specifically, the apparatus and the method are used to perform sequencing of the sample DNA by repeating a cycle including the steps of: inducing a DNA polymerase reaction by using four types of dNTP derivatives with detectable labels, which are captured as substrates of DNA polymerase in template DNA, and which can terminate a DNA chain extension reaction, with the presence of a protecting group; then detecting the captured dNTP derivatives on the basis of fluorescence or the like; and then returning the dNTP derivatives to an extension-capable state. Incidentally, since the above operation is based on a method of single molecule fluorescence detection, measurement is carried out in an environment such as a HEPA-filtered clean room.

Figure 1:
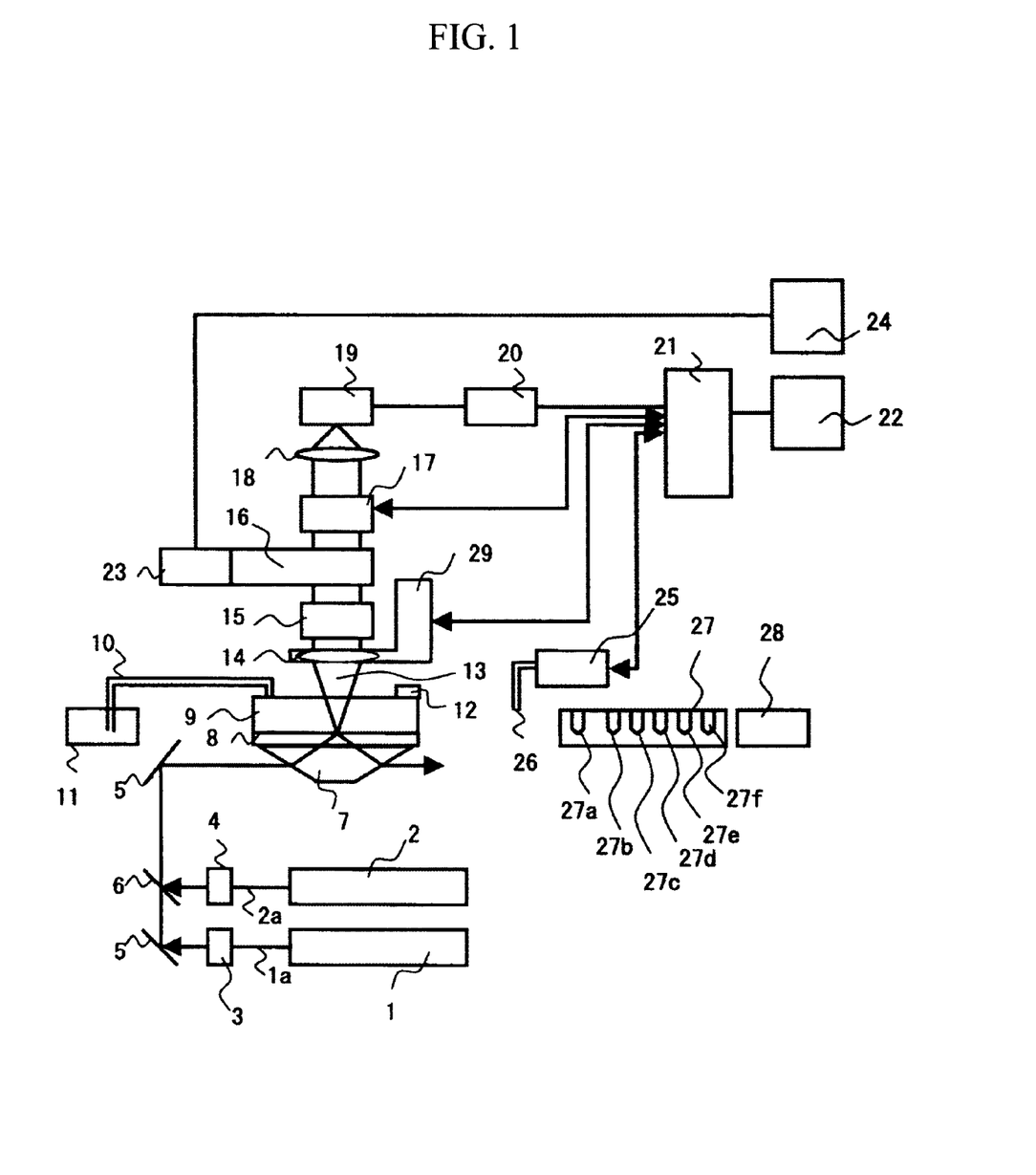
FIG. 1 is a configuration diagram of a DNA examination apparatus using a fluorescence analyzing method according to a first embodiment of the present invention.

FIG. 1 is a configuration diagram of a DNA examination apparatus using a fluorescence analyzing method according to the present invention. The apparatus has a configuration similar to that of a normal type (epifluorescence microscope) microscope, and performs fluorescence detection to measure an elongated state of DNA molecules trapped on a board 8. Incidentally, the apparatus may have a configuration similar to that of an inverted microscope.

Figure 2:
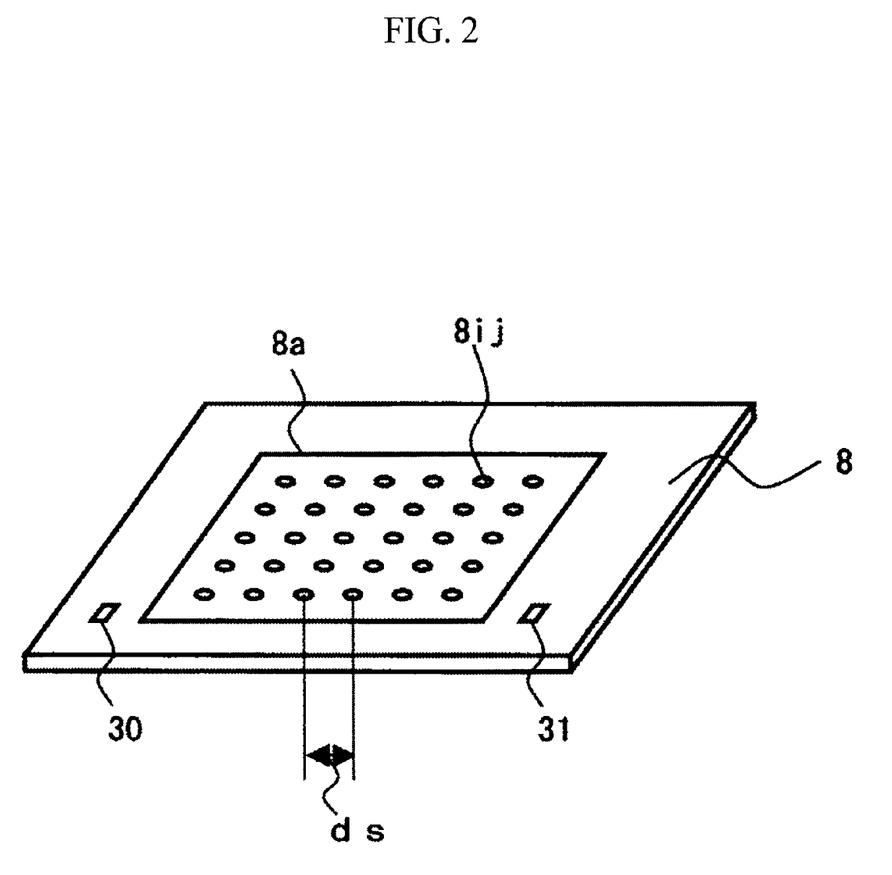
FIG. 2 is a view for explaining the structure of a board according to the first embodiment of the present invention.

The board 8 has a structure as shown in FIG. 2. The board 8 is made of a transparent material, for which synthetic quartz or the like can be used. The board 8 is provided with a reaction region 8a, with which a reagent or the like is brought into contact. In the reaction region 8a, plural regions 8ij to which DNA (oligonucleotide) is fixed. Each region 8ij has a diameter of 100 nm or less. Surfaces of the respective regions 8ij are treated for trapping DNA. For example, the surfaces are treated by bonding streptavidin to the regions 8ij, and then causing the regions 8ij to react with biotinylated DNA fragments. Thereby, DNA is trapped. DNA may also be trapped by treating the surface by immobilizing oligonucleotide of polythymidylic acid on the regions 8ij, then treating one end of DNA fragments to yield polyadenylic acid, and then producing a hybridization reaction. At this time, monomolecular DNA alone is allowed to enter each of the regions 8ij by appropriately preparing the concentration of the DNA fragments. One molecule can be trapped in each of the regions 8ij by making each region 8ij smaller. Hereinafter, description will be given of measurements made on the board under this condition. In the board formed in such a way, there might be monomolecular DNA in all the regions. Moreover, there might be monomolecular DNA only on a part of the regions 8ij. In this case, the region 8ij without DNA is empty. Note that an interval ds between each regions 8ij is set at 1 micron. A method for making the board having the regions spaced apart at equal intervals as mentioned above is carried out, for example, with an approach disclosed in Japanese Patent Application Laid-open Publication No. 2002-214142, or the like. Incidentally, the interval ds is greater than the size of each region 8ij, and is preferably about 1500 nm or less. The reaction region 8a of the board has the dimensions of 1 mm×1 mm, and the number of the regions 8ij is 1000000 (=1000× 1000).

"Cy3" (Trademark, Amersham) is used as the fluorescence label for dNTP. A fluorescent substance is not limited to Cy3, and various types of other fluorescent substances may be used. In the first embodiment, measurement is carried out by using one fluorescent substance, although four types of dNTP labeled respectively with different fluorescent substances may be used. Laser beam 1a emitted from a apparatus 1 for excitation of fluorescence (a YAG laser with a wavelength of 532 nm) is allowed to pass through a quarter-wave ($\lambda$/4) plate 3 to form circularly polarized light, which then enters a quartz prism 7 for illumination with total reflection, through a mirror 5, a dichroic mirror 6 and another mirror 5. Thereby, the substrate 8, on which DNA molecules are equidistantly trapped, is irradiated with the circularly polarized light from the back thereof. The quartz prism 7 is in contact with the board 8 with nonfluorescent glycerin interposed in between, and the laser beam is introduced to the board 8 without being reflected off the interface between the quartz prism 7 and the board 8. The laser beam is totally reflected by the surface of the board 8 at the incident angle on the board, ranging from about 66 to 68 degrees. Thereby, evanescent illumination is formed. This enables fluorescence measurement at a high S/N ratio. A region for this laser irradiation has a diameter of about 2 mm.

A temperature controller, although omitted from FIG. 1, is disposed in the vicinity of the board. The apparatus usually has a structure which allows illumination with halogen lamp from beneath the prism for the purpose of observation which structure is omitted in FIG. 1.

In addition to the laser apparatus 1, a laser apparatus 2 (a YAG laser with a wavelength of 355 nm) is disposed to allow laser to be irradiated coaxially with the laser beam 1a. The laser emitted from the laser apparatus 2 is used for the step of returning the dNTP derivatives to the extension-capable state, after performing the step of detecting the captured dNTP derivatives on the basis of the fluorescence.

A flow chamber 9 is disposed on top of the board 8, and is used for flowing the reagent or the like therethrough, and thereby for causing the reagent to undergo a reaction. The chamber has a reagent inlet 12. A dispensing unit 25 having a dispensing nozzle 26, a reagent storage unit 27 and a pipette tip box 28 for dispensing are used for processes such as pouring a target reagent solution. The reagent storage unit 27 is provided with a reagent solution container 27a, four types of dNTP-derivative-solution containers 27b, 27c, 27d and 27e, a cleaning fluid container 27f and so on. A dispensing tip in the tip box 28 is mounted to the dispensing nozzle 26, and is then used to suck an appropriate reagent solution. The sucked solution is then introduced to a reaction region of the board through the inlet of the chamber to thereby induce a reaction. Liquid waste is discharged into a liquid waste container 11 via a liquid drain tube 10. These operations are automatically performed by a control PC 21.

The flow chamber is made of a transparent material along the optical axis, and a fluorescence image is detected, as follows. Fluorescence 13 is focused by a condenser lens (an objective lens) 14 controlled with an autofocus apparatus 29. Then, fluorescence with required wavelengths is extracted with a filter unit 15. Thereby, a fluorescent image is detected with an auto-zoom mechanism 17, an imaging lens 18 and a two-dimensional sensor camera 19 (a high-sensitivity cooled CCD camera). The control PC 21 controls the settings of exposure time of the camera, the timing of capturing the fluorescent image, and the like, by use of a two-dimensional sensor camera controller 20. For using four types of dNTP, the apparatus may have such a configuration that the filter unit 15 switches the relevant filters for four types of fluorescent substances in the time-sharing manner, and thereby detects a fluorescent image.

For the purpose of adjustment or the like, the apparatus includes a lens-barrel 16 for transmitted light observation, a television camera 23 and a monitor 24, and thereby the apparatus allows observation of a state of the board 8 in real time, with halogen illumination or the like.

As shown in FIG. 2, register markers 30 and 31 are engraved on the board 8. The markers 30 and 31 are arranged parallel to the alignment of the regions 8$ij$, and a distance between the markers 30 and 31 is defined. Thus, the positions of the regions 8$ij$ can be calculated by detecting the markers by observation using transmitted illumination, and thereby the auto-zoom mechanism 17 can be controlled to specify a magnification. In the first embodiment, the two-dimensional sensor camera 19 (the high-sensitivity cooled CCD camera) having a pixel pitch (a pixel size) dd of 7.4 microns is used. When a magnification M of an imaging system is set at ×14.8, each interval between the regions 8$ij$ on the board 8 is divided in half for measurement.

A CCD area sensor is employed as the two-dimensional sensor camera used in the first embodiment. Specifically, a cooled CCD camera having a pixel size of 7.4×7.4 (microns) and 2048×2048 pixels is used. The reaction region 8$a$ of the board has the dimensions of 1 mm×1 mm, and the (1000× 1000) regions 8$ij$ are spaced apart from one another at intervals of 1 micron in the reaction region 8$a$. For performing measurement by using the cooled CCD camera with 2048× 2048 pixels, the magnification M of the imaging system is set at ×14.8, and thereby each pixel of the camera corresponds to (0.5×0.5) micron in terms of the reaction region. Besides the CCD area sensor, an image-pickup camera, such as a CMOS area sensor or the like, may be generally used as the two-dimensional sensor camera. Any one of two types of structures, which are a back illuminate type and a front illuminate type, can be used for the CCD area sensor. A CCD camera of an electron multiplication type having a function of signal multiplication inside an element, or the like, is effective in improving sensitivity. It is desirable that the sensor be of the cooled type. By setting the sensor at or below about −20 degrees, dark noise of the sensor can be reduced, and thus the accuracy in measurement can be improved.

In the first embodiment, a fluorescent image obtained from the reaction region 8$a$ is detected at once. However, the image may be detected as divided parts. When the size of the reaction region 8$a$ is increased to have dimensions of, for example, 5 mm×5 mm, a single image measurement cannot cover the entire region. Thus, the image is measured as divided into units of 1 mm×1 mm, and then the obtained plural images are recomposed to form the entire fluorescent image which is to be measured. In this case, an X-Y positioning mechanism for positioning the board is disposed under a stage, and then the control PC controls movements of the board to the position for irradiation, light irradiation, and fluorescent image detection. In the first embodiment, the X-Y positioning mechanism is not shown.

Various cameras can be used for measurement. In a case where a cooled CCD camera having a pixel size of 6.45×6.45 (μm) and 1392×1040 pixels is used, the magnification of the imaging system is adjusted to be 12.9. In a case where a camera having a pixel size of 9×9 (μm) and 4008×2672 pixels is used, the magnification of the imaging system is adjusted to be 18. In a case where a camera having a pixel size of 16×16 (μm) and 512×512 pixels is used, the magnification of the imaging system is adjusted to be 32.

Figure 3:
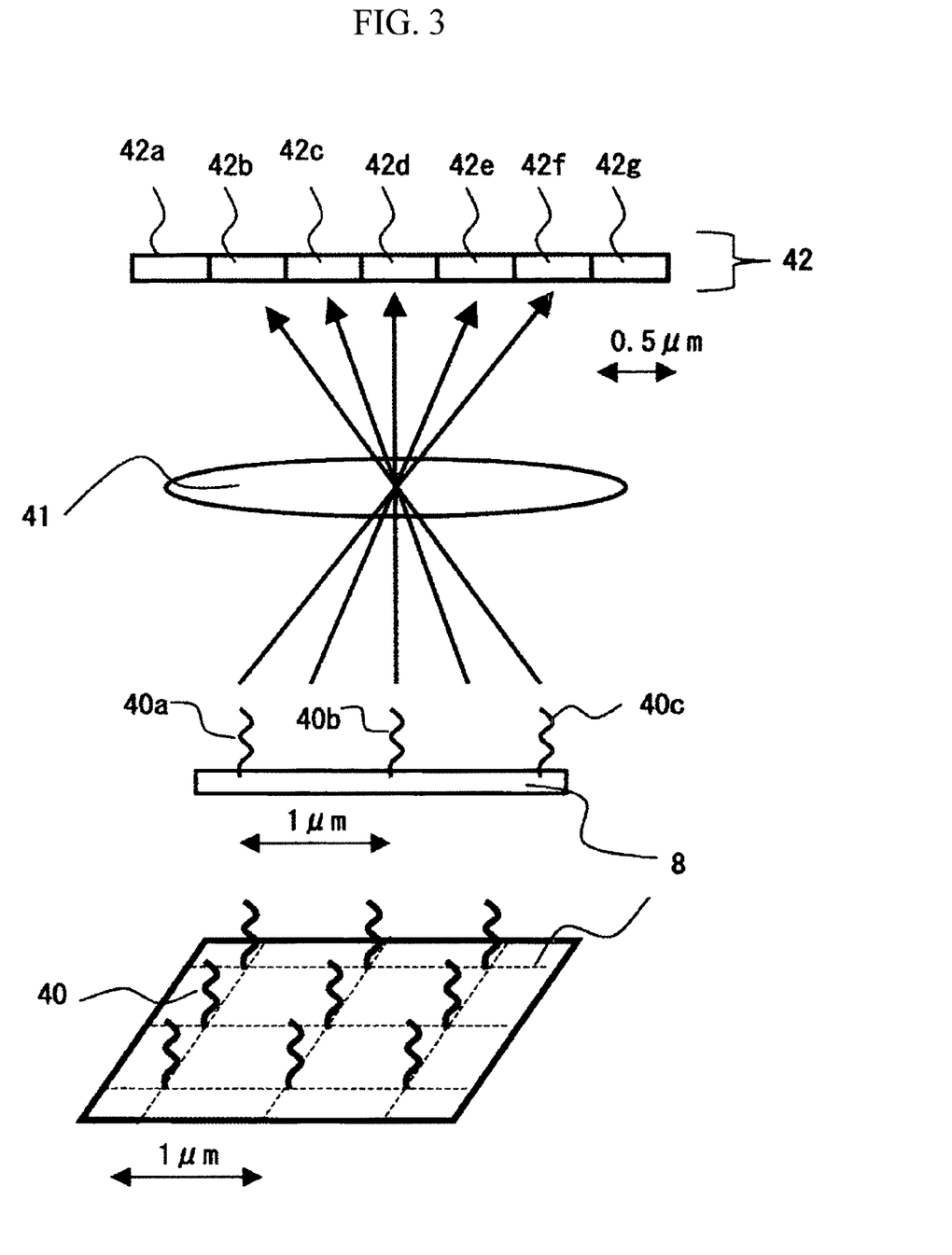
FIG. 3 is a view for explaining correspondences in image formation between the board and a two-dimensional sensor according to the first embodiment of the present invention.

FIG. 3 is a view for explaining correspondences in image formation between the board and the two-dimensional sensor according to the first embodiment. Description will be given with a supposition that single DNA molecules 40 (40$a$, 40$b$ and 40$c$) are trapped as spaced apart at intervals of 1 μm in a grid pattern on the board 8. Although the DNA molecules are in fact not necessarily trapped in all positions, the same effect is also achieved in such a case. Thus, the description will be given on the above supposition. An image is formed on pixels 42 of the two-dimensional sensor camera (the high-sensitivity cooled CCD camera) via a lens 41. For simplicity, FIG. 3 shows a situation where the magnification of the imaging system is set at 1 and the pixel pitch of the two-dimensional sensor camera is set at 1/14.8 (that is, the specification is standardized with the dimensions of the board.) The single DNA molecules 40$a$, 40$b$ and 40$c$ correspond to pixels 42$f$, 42$d$ and 42$b$, respectively, and thereby fluorescence can be detected from every other pixel. As a result, the fluorescence measurement is less affected by overlaps of fluorescence from the respective single DNA molecules 40$a$, 40$b$ and 40$c$, which overlaps are due to lens aberration, blurring of the image or the like, and is also less affected by ±10% deviation in positions where the single DNA molecules are trapped. Thus, the measurement can be performed stably.

Figure 4:
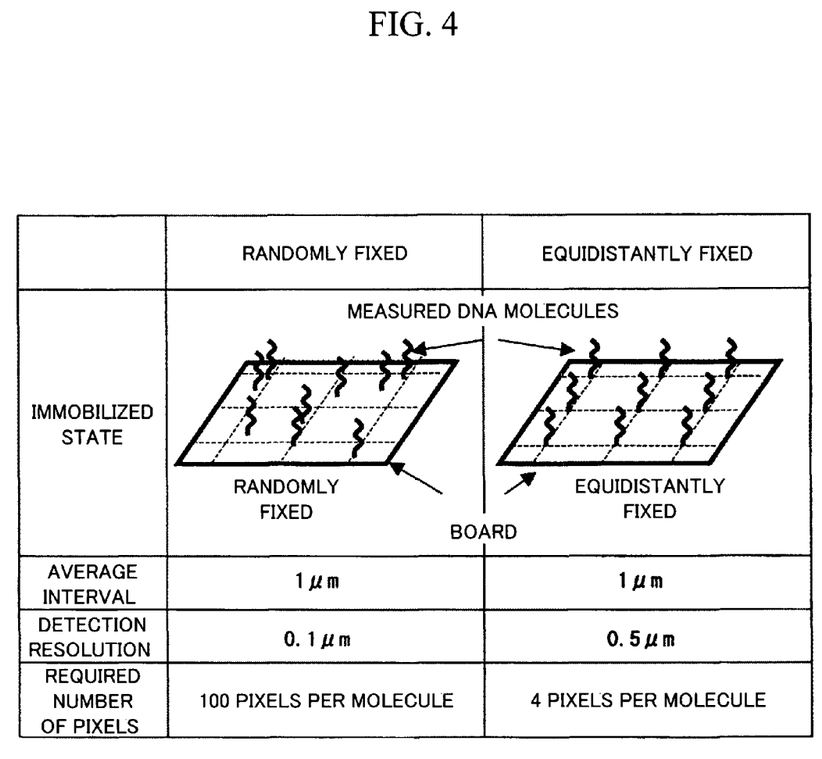
FIG. 4 is a table for explaining the effects of the first embodiment of the present invention.

FIG. 4 is a table for explaining the effects. A problem exists when DNA molecules are randomly trapped as has been conventional. Specifically, In a case of randomly trapping DNA molecules, as being performed with conventional techniques, even with the average intervals between the trapped molecules of 1 μm, some molecules are trapped as being stochastically close to one another while others are trapped as being stochastically away from one another. A fluorescent image needs to be detected at higher resolution in order to detect all these molecules as isolated from one another. However, the resolution is generally equivalent to 0.1 μm because of constraints due to the limitation on light diffraction, a limited number of pixels and the like. In this case as well, it is not possible to detect all of the trapped DNA molecules, or to detect the molecules individually, and about 10% of the DNA molecules may possibly overlap one another. Moreover, the average number of pixels required for the camera to detect each DNA molecule is 100, which is very inefficient. In contrast, advantageous effects are achieved when DNA molecules are equidistantly spaced. Specifically, as in the case of the first embodiment, when each interval between the molecules is divided in half, that is, measurement is carried out at a resolution of 0.5 μm, it suffices that the average number of four pixels be used for the camera to detect each DNA molecule, and thereby the measurement can be performed efficiently. This means that the measurement can be performed on 25 times as many molecules as those of a conventional case, and thus high throughput can be achieved with the measurement. In a case where measurement is performed on the same reaction region, the number of pixels to be used can be reduced, and thereby it is possible to reduce costs for the CCD. This also makes it possible to reduce the number of pixels, and hence the cost of the CCD, when measurements are made on the same reaction region.

In the case of the first embodiment, since a numerical aperture (NA) required for the condenser lens is about 0.67 and above, a dry lens can be used. Thus, the operation can be made easy.

Although the description has been given above of a case where each interval between the DNA molecules is divided in half for measurement, the same effect can be also achieved with each interval divided by 3. Furthermore, substantially the same effects can be achieved with each interval divided approximately by any integer between 1 and 5 inclusive.

Description will be given below of sequencing in accordance with an actual procedure for measurement. Fragments of M13-DNA are used as model samples. In accordance with normal practice, the end of the M13-DNA fragments is treated to form biotin. A biotinylated-DNA solution is held in the sample solution container 27a shown in FIG. 1, and Cy3-labeled caged dATP, caged dCTP, caged dGTP and caged dTTP solutions (including polymerase) are held in the containers 27b, 27c, 27d and 27e, respectively, shown in FIG. 1. Here, the Cy3-labeled caged dNTP is a caged compound of nucleotide bonded to a 2-nitrobenzyl group. The caged dNTP is captured as a complementary chain by polymerase. Meanwhile, the caged dNTP is inhibited from exhibiting the activity of its being continuously captured by a complementary chain synthesis reaction. For this reason, the caged dNTP elongates by 1 base, and then stops reacting. However, when the caged dNTP is then irradiated with ultraviolet with a wavelength of 360 nm or less, a caged substance (the 2-nitrobenzyl group) is liberated, and thereby the activity inherent in the nucleotide develops to induce the next synthesis of dNTP.

With the dispensing unit 25, the biotinylated-DNA to be a template is introduced into the flow chamber, and then is caused to react with the board. After cleaning the chamber, an oligoprimer is introduced so that the primer is hybridized with the biotinylated-DNA. Thereby, a complementary chain extension reaction occurs. After cleaning the chamber, the Cy3-labeled caged dATP solution is first introduced. When a base of the template next to the primer-bonded position is T, the Cy3-labeled caged dATP is captured. After cleaning the chamber, the caged dATP is irradiated with the laser beam 1a (the YAG laser with a wavelength of 532 nm), and then fluorescence is measured by the two-dimensional sensor camera. A determination can be made as to whether the Cy3-labeled caged dATP has been captured according to the presence or absence of the fluorescence. Subsequently, the chamber is cleaned, and then returned to an active state by irradiating the dATP with laser beam 2a (the YAG laser with a wavelength of 355 nm). The above procedure is executed for a cycle of the Cy3-labeled caged dCTP, caged dGTP and caged dTTP solutions. Sequencing can be accomplished by repeating the cycle plural times.

In the first embodiment, the fluorescence-labeled caged dNTP is used as the reagents which are the four types of dNTP derivatives with the detectable labels captured, as the substrates of the DNA polymerase, in the template DNA and capable of stopping the DNA chain extension reaction, with the presence of the protecting group. Here, the reagents make it possible to return the dNTP derivatives to the extension-capable state by use of certain means. However, a dNTP derivative formed of disulfide bonding of a fluorescent substance to nucleotide, or the like, may be used similarly perform the above sequencing. In this case, the extension stops with the presence of the fluorescent substance, while a tris(2-carboxyethyl)phosphine reagent or the like can be used to chemically dissociate the disulfide bond, and thereby to return the dNTP derivative to the extension-capable state.

Second Embodiment

Figure 5:
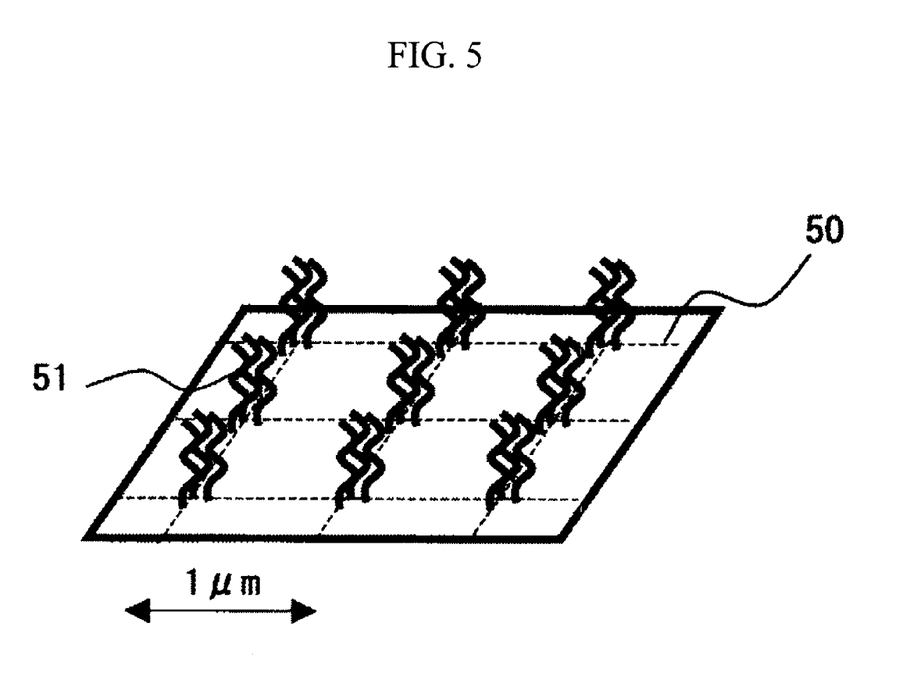
FIG. 5 is a view for explaining the structure of a board according to a second embodiment of the present invention.

The apparatus according to the first embodiment is configured so that each single DNA molecule individually enters the region 8ij. However, the apparatus may be configured so that groups 51 of DNA molecules are spaced apart at regular intervals on a board 50, as shown in FIG. 5. In this case, plural molecules of the same DNA fragments are captured in each of the region 8ij. The base extension reaction needs almost all molecules to be extended similarly. Therefore, the measurement needs enough reactive time. In the second embodiment, the plural molecules exist in each of the region 8ij. Therefore, because fluorescent strength grows, it becomes easy to detect. Moreover, even if the reaction of some molecules doesn't proceed when tens of thousands of molecules are fixed to each of the region 8ij, the influence of the sequencing on accuracy is a little. Therefore, the system can be composed at a low cost.

Third Embodiment

Figure 6:
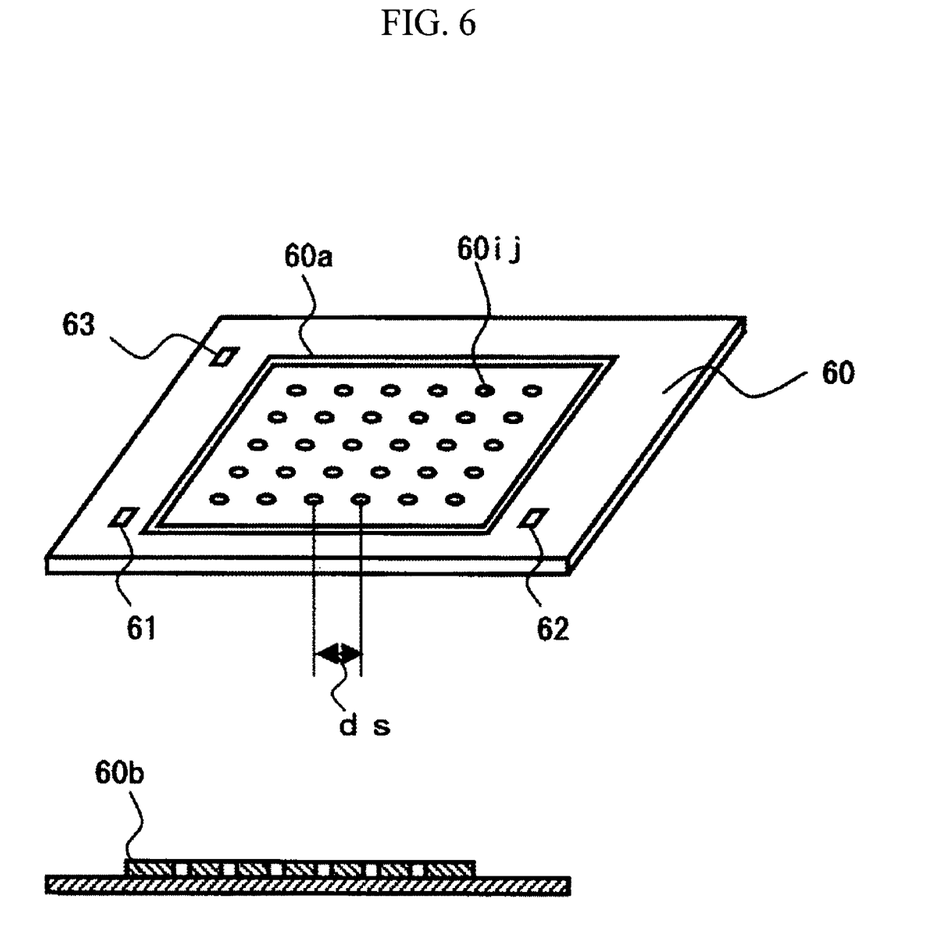
FIG. 6 is a view for explaining the structure of a board according to a third embodiment of the present invention.

Description will be given of an embodiment using another form of reaction region. FIG. 6 shows the structure of a board 60 according to the third embodiment. The board 60 has a structure including a reaction region 60a, plural regions 60ij which are formed in the reaction region 60a, and in which DNA is fixed, and an optically opaque mask 60b formed around the plural regions 60ij. Metal, such as aluminum or chromium, silicon carbide or the like, can be employed for a material of the mask. The material is formed into a thin film by vapor deposition or the like. Each region 60ij has a diameter of 100 nm or less. Methods for forming this opening in the mask 60b include vapor deposition using projection method (with which an appropriate mask is disposed between a deposition source and the board, to be subjected to vapor deposition), electron beam lithography and direct writing using photolithography.

The third embodiment makes it possible to achieve the same effects as those of the first embodiment. Moreover, according to the third embodiment, undesired stray light and fluorescence can be reduced since the region other than the regions 60ij is covered with the mask. Thus, it is made possible to perform measurement at higher sensitivity.

What is claimed is:

1. A fluorescence analyzing method comprising the steps of:
   irradiating a board, to which a plurality of oligonucleotides are fixed, with light for fluorescence measurement;
   focusing produced fluorescence to form an image; and
   detecting the fluorescence with a two-dimensional sensor, wherein:
   the board is provided with multiple regions to each of which is fixed one of the plurality of oligonucleotides,
   each region is spaced apart from an adjacent region on the board equidistantly in the vertical and horizontal directions,
   the following equation is satisfied:

$$dd = ds \times M/n$$

where ds denotes the distance between two adjacent regions, M denotes the imaging magnification of an optical focusing/imaging system, dd denotes the pixel pitch of the two-dimensional sensor, and n denotes an integer (n=1, 2, 3, 4, 5), and ds is between 100 nm and 10000 nm.

2. A fluorescence analyzing method comprising the steps of:
- irradiating a board, to which a plurality of oligonucleotides are fixed, with light for fluorescence measurement;
- focusing produced fluorescence to form an image; and
- detecting the fluorescence with a two-dimensional sensor, wherein:
- the board is provided with multiple regions,
- each region is spaced apart from an adjacent region equidistantly in the vertical and horizontal directions,
- a single oligonucleotide molecule is fixed to at least a part of each of the multiple regions or identical oligonucleotide molecules are fixed to at least a part of each of the multiple regions,
- the following equation is satisfied:

$$dd = ds \times M/n$$

where ds denotes the distance between adjacent regions, M denotes the imaging magnification of an optical focusing/imaging system, dd denotes the pixel pitch of the two-dimensional sensor, and n denotes an integer (n=1, 2, 3, 4, 5), and each region, has a diameter of 100 nm or less.

3. The fluorescence analyzing method according to any one of claims 1 and 2, wherein n=2, 3.

4. The fluorescence analyzing method according to any one of claims 1 and 2, wherein a film substance having an optical shield function is formed on a reaction region on the board, except for the multiple regions to which an oligonucleotide is fixed.

5. The fluorescence analyzing method according to claim 4, wherein the film substance is a metal film.

6. The fluorescence analyzing method according to any one of claims 1 and 2, wherein register markers are provided respectively to at least two positions on the board.

7. The fluorescence analyzing method according to any one of claims 1 and 2, comprising means for adjusting the imaging magnification M to satisfy the equation, dd=ds×M/n.

8. The fluorescence analyzing method according to claim 7, wherein the zooming function comprises means which automatically carries out the zooming according to a detection of the register markers.

9. A fluorescence analyzing method comprising the steps of:
- irradiating a board, to which a plurality of oligonucleotides are fixed, with light for fluorescence measurement;
- focusing produced fluorescence to form an image; and
- detecting the fluorescence with a two-dimensional sensor, wherein:
- the board is provided with multiple regions,
- each region is spaced apart from an adjacent region equidistantly in the vertical and horizontal directions,
- a single oligonucleotide molecule is fixed to each of at least a part of the multiple regions or identical oligonucleotide molecules are fixed to at least a part of each of the multiple regions,
- the following equation is satisfied:

$$dd = ds \times M/n$$

where ds denotes the distance between the adjacent regions, M denotes the imaging magnification of an optical focusing/imaging system, dd denotes the pixel pitch of the two-dimensional sensor, and n denotes an integer (n=1, 2, 3, 4, 5), and ds is between 100 nm and 10000 nm inclusive.

10. A fluorescence analyzing method comprising the steps of:
- irradiating a board, to which a plurality of oligonucleotides are fixed, with light for fluorescence measurement;
- focusing produced fluorescence to form an image; and
- detecting the fluorescence with a two-dimensional sensor, wherein:
- the board is provided with multiple regions,
- each region is spaced apart from an adjacent region equidistantly in the vertical and horizontal directions,
- the following equation is satisfied:

$$dd = ds \times M/n$$

where ds denotes the distance between adjacent regions, M denotes the imaging magnification of an optical focusing/imaging system, dd denotes the pixel pitch of the two-dimensional sensor, and n denotes an integer (n=1, 2, 3, 4, 5), and has a diameter of 100 nm or less.

* * * * *